(12) United States Patent
Nawaz et al.

(10) Patent No.: US 11,377,598 B2
(45) Date of Patent: Jul. 5, 2022

(54) METHOD RELATED TO HEAT TRANSFER FOR EXOTHERMIC REACTIONS

(71) Applicant: SABIC Global Technologies B.V., Bergen op Zoom (NL)

(72) Inventors: Zeeshan Nawaz, Riyadh (SA); Khalid Karim, Riyadh (SA); Jayen Barochia, Riyadh (SA)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 17/051,460

(22) PCT Filed: Apr. 25, 2019

(86) PCT No.: PCT/IB2019/053428
§ 371 (c)(1),
(2) Date: Oct. 29, 2020

(87) PCT Pub. No.: WO2019/215534
PCT Pub. Date: Nov. 14, 2019

(65) Prior Publication Data
US 2021/0054291 A1    Feb. 25, 2021

Related U.S. Application Data

(60) Provisional application No. 62/670,081, filed on May 11, 2018.

(51) Int. Cl.
*C10G 2/00* (2006.01)
(52) U.S. Cl.
CPC ....... *C10G 2/32* (2013.01); *C10G 2300/4081* (2013.01)
(58) Field of Classification Search
CPC ............. C10G 2/342; C10G 2/00; C10G 2/32
See application file for complete search history.

(56) References Cited

U.S. PATENT DOCUMENTS

| 2,846,421 A | 8/1958 | Pollock |
| 4,219,072 A | 8/1980 | Barlow, Sr. |
| 4,708,812 A | 11/1987 | Hatfield |
| 4,797,160 A | 1/1989 | Salyer |
| 4,971,605 A | 11/1990 | Tarman |
| 6,160,026 A | 12/2000 | Dai et al. |
| 6,400,896 B1 | 6/2002 | Longardner |
| 6,447,692 B1 | 9/2002 | Momoda et al. |
| 6,822,006 B1 | 11/2004 | O'Rear et al. |
| 9,416,067 B2 | 8/2016 | Karim et al. |
| 9,556,373 B2 | 1/2017 | Formato et al. |
| 2001/0021724 A1 | 9/2001 | Arcuri et al. |
| 2004/0132837 A1 | 7/2004 | Font Freide et al. |
| 2013/0056193 A1 | 3/2013 | Thiers |

FOREIGN PATENT DOCUMENTS

| CN | 103102868 A | 5/2013 |
| WO | WO1991006612 A1 | 5/1991 |

OTHER PUBLICATIONS

International Search Report and Written Opinion for PCT/IB2019/053428 dated Jul. 31, 2019, 11 pages.

*Primary Examiner* — Jafar F Parsa
(74) *Attorney, Agent, or Firm* — Norton Rose Fulbright US LLP

(57) ABSTRACT

Disclosed herein is a method of producing a product comprising C2-C5 hydrocarbons and C6-C18 hydrocarbons comprising the steps of: a) converting synthesis gas to the product comprising C2-C5 hydrocarbons and C6-C18 hydrocarbons in a first reactor; b) removing the product comprising C2-C5 hydrocarbons and C6-C18 hydrocarbons from the first reactor; c) reintroducing the C6-C18 hydrocarbons into the first reactor and/or introducing the C6-C18 hydrocarbons into a cooling jacket of the first reactor; and d) performing an exothermic reaction in the first reactor, thereby transferring heat from the exothermic reaction to the C6-C18 hydrocarbons, thereby storing heat in the C6-C18 hydrocarbons.

20 Claims, No Drawings

METHOD RELATED TO HEAT TRANSFER FOR EXOTHERMIC REACTIONS

CROSS-REFERENCE TO RELATED APPLICATIONS

This application is a national phase application under 35 U.S.C. § 371 of International Application No. PCT/IB2019/053428 filed Apr. 25, 2019, which claims priority to U.S. Provisional Patent Application No. 62/670,081 filed May 11, 2018. The entire contents of each of the above-referenced disclosures is specifically incorporated by reference herein without disclaimer.

FIELD

This invention relates to methods for performing chemical reactions to produce desired reaction products and, more particularly, to methods for controlling the temperature in exothermic reactions by utilizing highly conductive and/or phase change materials (e.g., syngas conversion reactions and use of products from such reactions in exothermic reactions).

BACKGROUND

Methods for conducting Fischer-Tropsch reactions and other exothermic reactions to produce a range of low-weight and higher-weight reaction products, such as lower hydrocarbons, lower olefins, higher olefins, higher paraffins, higher hydrocarbons, and wax are well known. However, the temperature of these exothermic reactions needs to be controlled cheaply and efficiently. There is a need in the art methods that provide temperature control over the exothermic reactions, in combination with heat removal.

Such methods that can be used to control the temperature of exothermic reactions, such as Fischer-Tropsch reactions for lower hydrocarbons, and enhance heat removal during the reaction is disclosed herein.

SUMMARY

Disclosed herein is a method of producing a product comprising C2-C5 hydrocarbons and C6-C18 hydrocarbons comprising the steps of: a) converting synthesis gas to the product comprising C2-C5 hydrocarbons and C6-C18 hydrocarbons in a first reactor; b) removing the product comprising C2-C5 hydrocarbons and C6-C18 hydrocarbons from the first reactor; c) reintroducing the C6-C18 hydrocarbons into the first reactor and/or introducing the C6-C18 hydrocarbons into a cooling jacket of the first reactor; and d) performing an exothermic reaction in the first reactor, thereby transferring heat from the exothermic reaction to the C6-C18 hydrocarbons, thereby storing heat in the C6-C18 hydrocarbons.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

Disclosed herein are materials, compounds, catalysts, compositions, and components that can be used for, can be used in conjunction with, can be used in preparation for, or are products of the disclosed method and compositions. It is to be understood that when combinations, subsets, interactions, groups, etc. of these materials are disclosed that while specific reference of each various individual and collective combinations and permutation of these compounds cannot be explicitly disclosed, each is specifically contemplated and described herein. For example, if a catalyst component is disclosed and discussed, and a number of alternative solid state forms of that component are discussed, each and every combination and permutation of the catalyst component and the solid state forms that are possible are specifically contemplated unless specifically indicated to the contrary. This concept applies to all aspects of this disclosure including, but not limited to, steps in methods of making and using the disclosed compositions. Thus, if there are a variety of additional steps that can be performed, it is understood that each of these additional steps can be performed with any specific aspect or combination of aspects of the disclosed methods, and that each such combination is specifically contemplated and should be considered disclosed.

In this specification and in the claims which follow, reference will be made to a number of terms which shall be defined to have the following meanings.

It must be noted that, as used in the specification and the appended claims, the singular forms "a," "an" and "the" include plural referents unless the context clearly dictates otherwise. Thus, for example, reference to "a catalyst support" includes mixtures of catalyst supports.

"Optional" or "optionally" means that the subsequently described event or circumstance can or cannot occur, and that the description includes instances where the event or circumstance occurs and instances where it does not.

As used herein, the terms "about" and "at or about" mean that the amount or value in question can be the value designated some other value approximately or about the same. It is generally understood, as used herein, that it is the nominal value indicated ±10% variation unless otherwise indicated or inferred. The term is intended to convey that similar values promote equivalent results or effects recited in the claims. That is, it is understood that amounts, sizes, formulations, parameters, and other quantities and characteristics are not and need not be exact, but can be approximate and/or larger or smaller, as desired, reflecting tolerances, conversion factors, rounding off, measurement error and the like, and other factors known to those of skill in the art.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The word "or" as used herein means any one member of a particular list and also includes any combination of members of that list.

Ranges can be expressed herein as from "" one particular value, and/or to "" another particular value. When such a range is expressed, another aspect includes from the one particular value and/or to the other particular value. Similarly, when values are expressed as approximations, by use of the antecedent ",", it will be understood that the particular value forms another aspect. It will be further understood that the endpoints of each of the ranges are significant both in relation to the other endpoint, and independently of the other endpoint.

References in the specification and concluding claims to parts by weight, of a particular element or component in a composition or article, denotes the weight relationship between the element or component and any other elements or components in the composition or article for which a part by weight is expressed. Thus, in a compound containing 2 parts by weight of component X and 5 parts by weight of component Y, X and Y are present at a weight ratio of 2:5, and are present in such a ratio regardless of whether additional components are contained in the compound.

A weight percent of a component, unless specifically stated to the contrary, is based on the total weight of the formulation or composition in which the component is included.

The transitional phrase "consist essentially of" or "essentially consist of" limits the scope of the disclosure to the specified materials or steps and those that do not materially affect the basic and novel characteristic(s) of the invention. As disclosed herein, the word "comprising" can be changed to "consist essentially of" or "essentially consist of". For example, if "a method comprising . . . " is disclosed, then "a method consisting essentially of . . . " is also disclosed.

The term "latent energy storage" or "latent heat storage" as defined herein is referenced to energy stored in a medium, such as C6-C18 hydrocarbons, as it changes phase, for example by the phase changes of solid-liquid or liquid-gas of C6-C18 hydrocarbons.

As used herein, an exothermic reaction is a chemical reaction that releases energy by light or heat. An endothermic reaction is a chemical reaction in which the system absorbs energy (i.e. heat). An exothermic reaction is the opposite of an endothermic reaction.

1. Methods

Efficient and reliable reactor systems for exothermic and endothermic reactions can remove heat, store heat, and release heat effectively. Phase change materials can assist with this, as their temperature increases as they absorb heat, but unlike conventional materials, when phase change materials reach the temperature at which they change phase (solid-to-liquid or liquid-to-gas) they absorb large amounts of heat without a significant increase in temperature. Thus, a phase change material, for example C6-C18 hydrocarbons, have superior thermal properties for heat transfer and absorption, as compared to other materials, for example, C2-C5 hydrocarbons, including C2-C5 olefins. When the temperature around a phase change material decreases, the phase change material changes phase again (liquid-to-solid or gas-to-liquid), releasing its stored latent heat.

Thus, there are advantages of using phase change materials to regulate exothermic or endothermic reactions due to their large heat storage capacity and their isothermal behavior during the charging and discharging process. However, while unloading a latent heat from a phase change material, the heat flux decreases due to phase change and enhance heat transfer.

Disclosed herein is a method of producing a product comprising C2-C5 hydrocarbons and C6-C18 hydrocarbons comprising the steps of: a) converting synthesis gas to the product comprising C2-C5 hydrocarbons and C6-C18 hydrocarbons in a first reactor; b) removing the product comprising C2-C5 hydrocarbons and C6-C18 hydrocarbons from the first reactor; c) reintroducing the C6-C18 hydrocarbons into the first reactor and/or introducing the C6-C18 hydrocarbons into a cooling jacket of the first reactor; and d) performing an exothermic reaction in the first reactor, thereby transferring heat from the exothermic reaction to the C6-C18 hydrocarbons, thereby storing heat in the C6-C18 hydrocarbons.

It is known how to convert synthesis gas to a product C2-C5 hydrocarbons and comprising C6-C18 hydrocarbons in a reactor. C2-C5 hydrocarbons cab be classified as lower hydrocarbons. The use of different catalysts can promote the formation of either lower hydrocarbons, such as C2-C5 hydrocarbons, including C2-C5 olefins, or higher hydrocarbons, such as C6-C18 hydrocarbons.

In one aspect, in step a), converting synthesis gas to the product comprising C2-C5 hydrocarbons and C6-C18 hydrocarbons in a first reactor is performed with a catalyst that selectively produces C2-C5 hydrocarbons, such as C2-C5 olefins, wherein the C6-C18 hydrocarbons are byproducts. The Anderson-Schulz-Flory (ASF) distribution of hydrocarbons makes it unavoidable that some amount of C6-C18 hydrocarbons are produced even when C2-C5 hydrocarbons are selectively produced. Such catalysts that selectively produces C2-C5 hydrocarbons, such as C2-C5 olefins, and C6-C18 hydrocarbons as byproducts are known in the art and can comprise Co and Mn, and optionally one or more additional promoter elements such as La, P, Na, K, Rb, Cs, Mg, Ca, Sr, Ba, Ti, or Zr. Such a catalyst is described in U.S. Pat. No. 9,416,067 to Karim, which is incorporated herein by reference, particularly for the disclosure of the CoMn based catalyst. Such a catalyst can be supported or un-supported.

The C6-C18 hydrocarbons have better heat transfer properties than C2-C5 hydrocarbons, which is taken advantage of in the methods disclosed herein.

The disclosed method efficiently remove and/or store heat. As described above, the C6-C18 hydrocarbons function as a coolant in step d). That is, the C6-C18 hydrocarbons absorbs heat from the exothermic reaction in step d), which in turn decreases the temperature in the reactor. The C6-C18 hydrocarbons is one of the products, produced in step a) and is a phase change material. Therefore, because C6-C18 hydrocarbons is one of the products, produced in step a) there are less separation steps needed of products produced in step a). The C6-C18 hydrocarbons can, for example, be used directly in step d) without separation and/or purification. For example, in one aspect, the method does not comprise a crystallization or precipitation step for separation of various products.

Step d) of performing an exothermic reaction in the first reactor, thereby transferring heat from the exothermic reaction to the C6-C18 hydrocarbons, thereby storing heat in the C6-C18 hydrocarbons can be performed from about 180° C. to about 320° C., at a pressure from about 1 bar to about 50 bar. For example, the step d) of performing an exothermic reaction in the first reactor, thereby transferring heat from the exothermic reaction to the C6-C18 hydrocarbons, thereby storing heat in the C6-C18 hydrocarbons can be performed from about 220° C. to about 260° C., at a pressure from about 5 bar to about 30 bar.

The C6-C18 hydrocarbons can either be recycled/maintained and used in the same first reactor they were produced in, or they can be used in another reactor, such as a second reactor. In one aspect, the C6-C18 hydrocarbons are reintroduced into the first reactor. In another aspect, the C6-C18 hydrocarbons are maintained into the first reactor. In another aspect, the C6-C18 hydrocarbons are introduced into a second reactor.

In one aspect, the C6-C18 hydrocarbons can be introduced into the cooling jacket of the first reactor. In this aspect, heat is absorbed by the C6-C18 hydrocarbons from the walls of the cooling jacket which is in contact with the reactor performing the exothermic reaction of step d).

In one aspect, the C6-C18 hydrocarbons are reintroduced into the first reactor with the reactants of the exothermic reaction. Accordingly, in one example, the C6-C18 hydrocarbons can be added to the first reactor prior to the addition of the reactants. In another example, the C6-C18 hydrocarbons can be added to the first reactor prior to the addition of the reactants. In yet another example, the C6-C18 hydrocarbons can be mixed with the reactants of the exothermic reaction. The C6-C18 hydrocarbons will also improve thermal properties of the fluid and enhance thermal conductivity. For example the C6-C18 hydrocarbons can mixed with the reactants of the exothermic reaction prior to introduction to the reactor.

In one aspect, the method further comprises after step d) performing an endothermic reaction in the first reactor, thereby transferring heat from the C6-C18 hydrocarbons with the stored heat to the endothermic reaction. Thus, the energy stored in the C6-C18 hydrocarbons is released with the endothermic reaction to drive the endothermic reaction. As such, the energy released with the exothermic reaction can be used to drive the endothermic reaction by the energy storage capabilities of the C6-C18 hydrocarbons.

In one aspect, the conditions for the endothermic reaction is such that the transferring of heat from the C6-C18 hydrocarbons with the stored heat to the endothermic reaction causes a phase change of the C6-C18 hydrocarbons. Thus, the phase change of the C6-C18 hydrocarbons releases heat to drive the endothermic reaction.

In one aspect, the method can further comprise after step d) transferring the C6-C18 hydrocarbons with the stored heat from the first reactor to a second reactor and performing an endothermic reaction in the second reactor, thereby transferring heat from the C6-C18 hydrocarbons with the stored heat to the endothermic reaction. Thus, the heat is stored in the C6-C18 hydrocarbons and can be transferred from one reactor to another, and the phase change of the C6-C18 hydrocarbons releases heat to drive the endothermic reaction in the second reactor.

In one aspect, the method can further comprise after the endothermic reaction, transferring the C6-C18 hydrocarbons from the second reactor back to the first reactor and performing an exothermic reaction in the first reactor, thereby transferring heat from the exothermic reaction to the C6-C18 hydrocarbons, thereby storing heat in the C6-C18 hydrocarbons. Thus, the C6-C18 hydrocarbons can be recycled one or more times within the same reactor, or between different reactors, such as a first reactor and a second reactor. The recycling of the C6-C18 hydrocarbons and the alternation of subjecting the C6-C18 hydrocarbons to temperatures associated with exothermic reactions and endothermic reactions allows for the C6-C18 hydrocarbons to be used multiple times.

In one aspect, the C6-C18 hydrocarbons can comprise C6-C15, C6-C12, or C6-C9 hydrocarbons. In another aspect, the C6-C18 hydrocarbons can comprise C9-C18, C12-C18, or C15-C18 hydrocarbons. The composition of the C6-C18 hydrocarbons can influence the temperature at which the C6-C18 hydrocarbons goes through the phase change and/or enhance thermal conductivity of fluid in the system. In general the phase change occurs at a higher temperature as the number of carbons increases in the hydrocarbons.

In one aspect, the C2-C5 hydrocarbons can comprise C2-C5 olefins. As described above, the C2-C5 olefins can be selectively produced by CoMn based catalyst.

In one aspect, the method can further comprise separating the C2-C5 hydrocarbons, for example C2-C5 olefins, from the C6-C18 hydrocarbons prior to step c). Techniques to separate higher hydrocarbons, such as C6-C18 hydrocarbons, from lower hydrocarbons, such as C2-C5 hydrocarbons or C2-C5 olefins. For example, distillation columns, membranes, or swing absorption techniques can be used to separate higher hydrocarbons, such as C6-C18 hydrocarbons, from lower hydrocarbons, such as C2-C5 hydrocarbons or C2-C5 olefins. In one example, distillation columns can be used to separate higher hydrocarbons, such as C6-C18 hydrocarbons, from lower hydrocarbons, such as C2-C5 hydrocarbons or C2-C5 olefins.

In one aspect, wherein the exothermic reaction in step d) converts synthesis gas to C2-C5 hydrocarbons. The exothermic reaction in step d) can be a Fischer-Tropsch reaction. The reaction in step a) and step d) can be identical in the use of catalysts, reactants and reaction conditions.

Methods for producing synthesis gas (or syngas) from natural gas, coal, or waste streams or biomass, at almost any desired ratio of hydrogen to carbon monoxide are well known to those of ordinary skill in the art. A large range of ratios of hydrogen to carbon monoxide can be suitable for the practice of the current invention, but since high conversion of carbon monoxide to hydrocarbons is desired, syngas mixtures comprising at least equimolar ratios of hydrogen to carbon monoxide or higher are typically employed, i.e. from 3:1 $H_2/CO$ to 1:1 $H_2/CO$. In some aspects, the ratios of hydrogen to carbon monoxide employed are from 2:1 $H_2/CO$ to 1:1 $H_2/CO$. Optionally, inert or reactive carrier gases, such as $N_2$, $CO_2$, methane, ethane, propane, and the like can be contained in and/or mixed with the syngas.

The syngas is typically forced to flow through reactors comprising the solid catalysts, wherein the reactors are designed to retain the catalyst against the vapor phase flow of syngas, at temperatures sufficient to maintain most of the hydrocarbon products of the catalytic reactions in the vapor phase at the selected operating pressures. The catalyst particles can be packed into a fixed bed, or dispersed in a fluidized bed, or in other suitable arrangements known to those of ordinary skill in the art.

In one aspect, the syngas is contacted with a catalyst at a temperature of at least 150° C., or at least 200° C., and at a temperature below 400° C. or from a temperature of 180° C. to 320° C., or from a temperature of 220° C. to 260° C.

In one aspect, the syngas is contacted with the catalyst at a pressure of at least 3 bar, 5 bar, or at least, 10 bar, or at least 15 bar, or at least 25 bar, or at least 50 bar, or at least 75 bar, and less than 200 bar, or less than 100 bar. In many aspects of the methods of the reaction, the syngas is contacted with the catalyst compositions at a pressure from 5 bar to 100 bar. In some aspects of the methods of the reaction, the syngas is contacted with the catalyst at a pressure from about 3 bar to about 15 bar. In some aspects of the methods of the reaction, the syngas is contacted with the catalyst at a pressure from about 5 bar to about 30 bar.

In one aspect, the syngas is contacted with the catalyst to produce relatively high conversions of the carbon monoxide present in syngas. In one aspect, conversion of carbon monoxide is at least 60%, at least 65%, at least 67%, at least 70%, at least 73%, or at least 75%. In one aspect, less than 30%, or less than 25% of the carbon monoxide fed to the reactors is converted to $CO_2$.

In one aspect of the methods of the reaction, the syngas is contacted with a catalyst at such a rate and/or in such a way as to produce relatively high conversions of the syngas and/or high conversions of carbon monoxide. In another aspect of the methods, at least 5 mole %, 10 mole %, 20 mole %, 30 mole % 40 mole %, at least 50 mole %, at least 60 mole %, at least 70 mole %, or at least 80 mole %, or at least 90 mole %, or at least mole 95% of the CO in syngas is converted to C6-C18 hydrocarbons in step a). For example, from 5 mole % to 50 mole % of the CO in syngas is converted to C6-C18 hydrocarbons in step a). In another example, from 5 mole % to 30 mole % of the CO in syngas is converted to C6-C18 hydrocarbons in step a). In yet another example, from 20 mole % to 50 mole % of the CO in syngas is converted to C6-C18 hydrocarbons in step a).

Optionally, in various aspects, the disclosed methods can be operated or performed on equipment of an industrial scale or pilot scale. For example, the disclosed methods can be operated or performed on equipment of an industrial scale. In one aspect, the methods disclosed herein can be configured to produce the disclosed reaction products on an industrial scale. For example, according to further aspects, the methods can produce batches of one or more of the disclosed reaction products on an industrial scale. In a further aspect, the batch size can comprise any desired industrial-scale batch size. It is contemplated that the batch capacity of the reactor can vary due to vessel size and the amount of loaded catalyst. The reactor capacity can also be related to catalyst activity, type of catalyst, and the choice of reactor. In exemplary aspects, catalyst volume per reactor and feed flow rate can vary from about 0.1 $m^3$ to about 500 $m^3$.

In various aspects, the disclosed and methods can be operated or performed on any desired time scale or production schedule that is commercially practicable. It is contemplated that the reactor of steps a) and d) can be configured for continuous, semi batch, or batch wise operation. The residence time and/or weight hourly space velocity (WHSV) can vary depending upon the choice and performance of catalyst and the nature of the chemical reaction. Similarly, the production rate of desired product can also vary. In exemplary syngas conversion reactions, WHSV and residence time can respectively vary between about 100 and about 10,000 Nl/kg/hr and from about 1 to about 50 seconds. In these aspects, the productivity of such a syngas conversion reaction for hydrocarbons can vary between about 0.01 and about 100 kg/kg of Catalyst/hr. However, it is contemplated that the productivity of the reaction can vary further depending upon the choice and performance of catalyst.

In additional aspects, the components used in the disclosed methods e shaped and sized to permit production of the disclosed reaction products on an industrial scale. Similarly, it is contemplated that the components used in the disclosed methods can comprise materials having material properties that are configured to permit production of the disclosed reaction products on an industrial scale. In further aspects, the components in the disclosed methods can be shaped and sized to produce the desired reaction products in accordance with the desired time scale or production schedule.

In further exemplary aspects, it is contemplated that the components used in the disclosed methods can comprise any conventional materials that are capable of receiving, contacting reactants and products, and the like as disclosed herein.

2. Aspects

In view of the described catalyst and catalyst compositions and methods and variations thereof, herein below are described certain more particularly described aspects of the inventions. These particularly recited aspects should not however be interpreted to have any limiting effect on any different claims containing different or more general teachings described herein, or that the "particular" aspects are somehow limited in some way other than the inherent meanings of the language and formulas literally used therein.

Aspect 1: A method of producing a product comprising C2-C5 hydrocarbons and C6-C18 hydrocarbons comprising the steps of: a) converting synthesis gas to the product comprising C2-C5 hydrocarbons and C6-C18 hydrocarbons in a first reactor; b) removing the product comprising C2-C5 hydrocarbons and C6-C18 hydrocarbons from the first reactor; c) reintroducing the C6-C18 hydrocarbons into the first reactor and/or introducing the C6-C18 hydrocarbons into a cooling jacket of the first reactor; and d) performing an exothermic reaction in the first reactor, thereby transferring heat from the exothermic reaction to the C6-C18 hydrocarbons, thereby storing heat in the C6-C18 hydrocarbons.

Aspect 2: The method of aspect 1, wherein the transferring of heat from the exothermic reaction to the C6-C18 hydrocarbons causes a phase change of the C6-C18 hydrocarbons.

Aspect 3: The method of aspects 1 or 2, wherein the C6-C18 hydrocarbons are reintroduced into the first reactor.

Aspect 4: The method of any one of aspects 1-3, wherein the C6-C18 hydrocarbons are introduced into the cooling jacket of the first reactor.

Aspect 5: The method of any one of aspects 1-4, wherein the C6-C18 hydrocarbons are reintroduced into the first reactor with the reactants of the exothermic reaction.

Aspect 6: The method of any one of aspects 1-5, wherein the C6-C18 hydrocarbons are mixed with the reactants of the exothermic reaction.

Aspect 7: The method of any one of aspects 1-6, wherein the method further comprises after step d) performing an endothermic reaction in the first reactor, thereby transferring heat from the C6-C18 hydrocarbons with the stored heat to the endothermic reaction.

Aspect 8: The method of aspect 7, wherein the transferring of heat from the C6-C18 hydrocarbons with the stored heat to the endothermic reaction causes a phase change of the C6-C18 hydrocarbons.

Aspect 9: The method of aspect 1, wherein the method further comprises after step d) transferring the C6-C18 hydrocarbons with the stored heat from the first reactor to a second reactor and performing an endothermic reaction in the second reactor, thereby transferring heat from the C6-C18 hydrocarbons with the stored heat to the endothermic reaction.

Aspect 10: The method of aspect 9, wherein the method further comprises after the endothermic reaction, transferring the C6-C18 hydrocarbons from the second reactor back to the first reactor and performing an exothermic reaction in the first reactor, thereby transferring heat from the exothermic reaction to the C6-C18 hydrocarbons, thereby storing heat in the C6-C18 hydrocarbons.

Aspect 11: The method of any one of aspects 1-10, wherein the C2-C5 hydrocarbons comprises C2-C5 olefins.

Aspect 12: The method of aspect 11, wherein the method further comprises separating the C2-C5 olefins from the C6-C18 hydrocarbons prior to step c).

Aspect 13: The method of any one of aspects 1-12, wherein the exothermic reaction in step d) converts synthesis gas to C2-C5 hydrocarbons.

Aspect 14: The method of any one of aspects 1-13, wherein step a) converts synthesis gas to C6-C18 hydrocarbons as by-products.

Aspect 15: The method of any one of aspects 1-14, wherein the exothermic reaction in step d) selectively converts synthesis gas to C2-C5 olefins.

Aspect 16: The method of any one of aspects 1-15, wherein step a) selectively converts synthesis gas to C2-C5 olefins.

Aspect 17: The method of any one of aspects 1-16, wherein the method does not include the use of a salt-based product or a molten metal produce as a phase change material.

Aspect 18: The method of any one of aspects 1-17, wherein the method is performed on an industrial and pilot scale.

Aspect 19: The method of any one of aspects 1-18, wherein the C6-C18 hydrocarbons comprise C6-C12 hydrocarbons.

Aspect 20: The method of any one of aspects 1-19, wherein step a) comprises contacting synthesis gas with a catalyst comprising Co and Mn.

What is claimed is:

1. A method of producing a product comprising C2-C5 hydrocarbons and C6-C18 hydrocarbons comprising the steps of:
   a) converting synthesis gas to the product comprising C2-C5 hydrocarbons and C6-C18 hydrocarbons in a first reactor;
   b) removing the product comprising C2-C5 hydrocarbons and C6-C18 hydrocarbons from the first reactor;
   c) reintroducing the C6-C18 hydrocarbons into the first reactor and/or introducing the C6-C18 hydrocarbons into a cooling jacket of the first reactor; and
   d) performing an exothermic reaction in the first reactor, thereby transferring heat from the exothermic reaction to the C6-C18 hydrocarbons, thereby storing heat in the C6-C18 hydrocarbons;
   wherein the transferring of heat from the exothermic reaction to the C6-C18 hydrocarbons causes a phase change of the C6-C18 hydrocarbons;
   and wherein the syngas is contacted with a catalyst at a temperature of from and a pressure of 75 bar to less than 200 bar.

2. The method of claim 1, wherein the syngas is contacted with a catalyst at a temperature of from 180° C. to 320° C. and a pressure of from 5 bar to 100.

3. The method of claim 1, wherein the syngas is contacted with a catalyst at a temperature of 180° C. and a pressure of 100 bar to less than 200 bar.

4. The method of claim 1, wherein the C6-C18 hydrocarbons are introduced into the cooling jacket of the first reactor.

5. The method of claim 1, wherein the C6-C18 hydrocarbons are reintroduced into the first reactor with the reactants of the exothermic reaction.

6. The method of claim 1, wherein the C6-C18 hydrocarbons are mixed with the reactants of the exothermic reaction; and wherein the catalyst comprises Co and Mn, and each of promoter elements La, P, Na, K, Rb, Cs, Mg, Ca, Sr, Ba, Ti and Zr.

7. The method of claim 1, wherein the catalyst comprises Co and Mn, and at least one promoter element selected form the group consisting of La, P, Na, K, Rb, Cs, Mg, Ca, Sr, Ba, Ti and Zr.

8. The method of claim 7, wherein the promoter element is La.

9. The method of claim 7, wherein the promoter element is P.

10. The method of claim 7, wherein the promoter element is Cs.

11. The method of claim 7, wherein the promoter element is Na.

12. The method of claim 7, wherein the promoter element is K.

13. The method of claim 7, wherein the promoter element is Rb.

14. The method of claim 7, wherein the promoter element is Cs.

15. The method of claim 7, wherein the promoter element is Mg.

16. The method of claim 7, wherein the promoter element is Ca.

17. The method of claim 7, wherein the promoter element is Sr.

18. The method of claim 7, wherein the promoter element is Ba.

19. The method of claim 7, wherein the promoter element is Zr.

20. A method of producing a product comprising C2-C5 hydrocarbons and C6-C18 hydrocarbons, the method consisting of the steps of:
   a) converting synthesis gas to the product comprising C2-C5 hydrocarbons and C6-C18 hydrocarbons in a first reactor;
   b) removing the product comprising C2-C5 hydrocarbons and C6-C18 hydrocarbons from the first reactor;
   c) reintroducing the C6-C18 hydrocarbons into the first reactor and/or introducing the C6-C18 hydrocarbons into a cooling jacket of the first reactor; and
   d) performing an exothermic reaction in the first reactor, thereby transferring heat from the exothermic reaction to the C6-C18 hydrocarbons, thereby storing heat in the C6-C18 hydrocarbons, wherein step a) comprises contacting synthesis gas with a catalyst comprising Mn;
   wherein the transferring of heat from the exothermic reaction to the C6-C18 hydrocarbons causes a phase change of the C6-C18 hydrocarbons;
   wherein the C6-C18 hydrocarbons are reintroduced into the first reactor;
   wherein the C6-C18 hydrocarbons are introduced into the cooling jacket of the first reactor;
   wherein the C6-C18 hydrocarbons are reintroduced into the first reactor with the reactants of the exothermic reaction.
   wherein the C6-C18 hydrocarbons are mixed with the reactants of the exothermic reaction;
   wherein the method further comprises after step d) performing an endothermic reaction in the first reactor, thereby transferring heat from the C6-C18 hydrocarbons with the stored heat to the endothermic reaction;
   wherein the transferring of heat from the C6-C18 hydrocarbons with the stored heat to the endothermic reaction causes a phase change of the C6-C18 hydrocarbons;
   wherein the method further comprises after step d) transferring the C6-C18 hydrocarbons with the stored heat from the first reactor to a second reactor and performing an endothermic reaction in the second reactor, thereby transferring heat from the C6-C18 hydrocarbons with the stored heat to the endothermic reaction;

wherein the method further comprises after the endothermic reaction, transferring the C6-C18 hydrocarbons from the second reactor back to the first reactor and performing an exothermic reaction in the first reactor, thereby transferring heat from the exothermic reaction to the C6-C18 hydrocarbons, thereby storing heat in the C6-C18 hydrocarbons;

wherein the C2-C5 hydrocarbons comprises C2-C5 olefins;

wherein the method further comprises separating the C2-C5 olefins from the C6-C18 hydrocarbons prior to step c);

wherein the exothermic reaction in step d) converts synthesis gas to C2-C5 hydrocarbons;

wherein step a) converts synthesis gas to C6-C18 hydrocarbons as by-products;

wherein the exothermic reaction in step d) selectively converts synthesis gas to C2-C5 olefins;

wherein step a) selectively converts synthesis gas to C2-C5 olefins;

wherein the method does not include the use of a salt-based product or a molten metal produce as a phase change material;

wherein the method is performed on an industrial and pilot scale;

wherein the syngas is contacted with a catalyst at a temperature of 180° C. and a pressure of syngas is contacted with a catalyst at a pressure of 100 bar to less than 200 bar;

wherein the catalyst comprises Co and Mn, and each of promoter elements La, P, Na, K, Rb, Cs, Mg, Ca, Sr, Ba, Ti and Zr; and wherein the C6-C18 hydrocarbons comprise C6-C12 hydrocarbons.

* * * * *